(12) United States Patent
Felt et al.

(10) Patent No.: US 7,833,185 B2
(45) Date of Patent: Nov. 16, 2010

(54) APPARATUS FOR SEPARATING A VOLUME OF WHOLE BLOOD INTO AT LEAST THREE COMPONENTS

(75) Inventors: Thomas Felt, Boulder, CO (US); Brian M. Holmes, Lakewood, CO (US); Bruce Gibbs, Arvada, CO (US)

(73) Assignee: CaridianBCT, Inc., Lakewood, CO (US)

( * ) Notice: Subject to any disclaimer, the term of this patent is extended or adjusted under 35 U.S.C. 154(b) by 310 days.

(21) Appl. No.: 11/741,081

(22) Filed: Apr. 27, 2007

(65) Prior Publication Data

US 2007/0203444 A1    Aug. 30, 2007

Related U.S. Application Data

(63) Continuation of application No. PCT/US2005/044821, filed on Dec. 12, 2005.

(60) Provisional application No. 60/639,497, filed on Dec. 28, 2004.

(51) Int. Cl.
*A61M 37/00* (2006.01)

(52) U.S. Cl. .................................... 604/6.02; 604/6.01

(58) Field of Classification Search ................ 604/4.01, 604/5.01, 6.01, 6.02–6.04, 6.05, 6.15, 406, 604/408, 410; 210/781, 782; 422/44
See application file for complete search history.

(56) References Cited

U.S. PATENT DOCUMENTS

| 3,297,244 A | 1/1967 | Hein |
| 3,326,458 A | 6/1967 | Merman et al |
| 3,679,128 A | 7/1972 | Unger et al. |
| 3,708,110 A | 1/1973 | Unger et al. |
| 3,724,747 A | 4/1973 | Unger et al. |
| 3,737,096 A | 6/1973 | Jones et al. |
| 3,858,796 A | 1/1975 | Unger et al. |
| 3,987,961 A | 10/1976 | Sinn et al. |
| 4,146,172 A | 3/1979 | Cullis et al. |

(Continued)

FOREIGN PATENT DOCUMENTS

DE    2545283 A1    4/1977

(Continued)

OTHER PUBLICATIONS

EP Application No. 05077728.3-2310, "Extended Search Report", Sep. 18, 2006.

(Continued)

*Primary Examiner*—Tatyana Zalukaeva
*Assistant Examiner*—Benedict L Hanrahan
(74) *Attorney, Agent, or Firm*—Edna M. O'Connor; John R. Merkling; Laura B. Arcinioga (57) ABSTRACT

A method and apparatus for separating a volume of whole blood contained in a separation bag into at least three components comprising centrifuging the separation bag so as to separate therein a first inner layer comprising plasma, a second intermediate layer comprising platelets, a third intermediate layer comprising lymphocytes, monocytes and granulocytes and a fourth outer layer comprising red blood cells, transferring, into a plasma component bag connected to the separation bag, a plasma component and transferring into a mononuclear cell component bag a mononuclear cell components.

4 Claims, 5 Drawing Sheets

U.S. PATENT DOCUMENTS

| | | | |
|---|---|---|---|
| 4,389,207 A | 6/1983 | Bacehowski et al. | |
| 4,405,079 A | 9/1983 | Schoendorfer | |
| 4,421,503 A | 12/1983 | Latham, Jr. et al. | |
| 4,482,342 A | 11/1984 | Lueptow et al. | |
| 4,720,284 A | 1/1988 | McCarty | |
| 4,850,995 A | 7/1989 | Tie et al. | |
| 4,990,132 A | 2/1991 | Unger et al. | |
| 5,114,396 A | 5/1992 | Unger et al. | |
| 5,427,695 A | 6/1995 | Brown | |
| 5,543,062 A | 8/1996 | Nishimura | |
| 5,632,906 A | 5/1997 | Ishida et al. | |
| 5,637,082 A | 6/1997 | Pages et al. | |
| 5,651,766 A * | 7/1997 | Kingsley et al. | 604/6.04 |
| 5,670,060 A * | 9/1997 | Matkovich et al. | 210/767 |
| 5,723,050 A | 3/1998 | Unger et al. | |
| 5,738,644 A | 4/1998 | Holmes et al. | |
| 5,874,208 A | 2/1999 | Unger | |
| 5,904,355 A | 5/1999 | Powers et al. | |
| 5,964,724 A | 10/1999 | Rivera et al. | |
| 6,039,711 A | 3/2000 | Headley et al. | |
| 6,106,727 A * | 8/2000 | Krasnoff et al. | 210/739 |
| 6,261,217 B1 | 7/2001 | Unger et al. | |
| 6,296,602 B1 | 10/2001 | Headley | |
| 6,315,706 B1 | 11/2001 | Unger et al. | |
| 6,348,031 B1 | 2/2002 | Unger et al. | |
| 6,439,577 B2 | 8/2002 | Jorgensen et al. | |
| 6,558,307 B2 | 5/2003 | Headley | |
| 6,605,223 B2 * | 8/2003 | Jorgensen et al. | 210/745 |
| 6,610,002 B2 * | 8/2003 | Dolecek | 494/37 |
| 6,641,552 B1 | 11/2003 | Kingsley et al. | |
| 6,656,105 B2 | 12/2003 | Hogberg et al. | |
| 6,835,316 B2 * | 12/2004 | Dolecek | 210/787 |
| 7,347,932 B2 * | 3/2008 | Holmes et al. | 210/104 |
| 2001/0051569 A1 | 12/2001 | Headley | |
| 2002/0020680 A1 * | 2/2002 | Jorgensen | 210/782 |
| 2002/0119880 A1 | 8/2002 | Hogberg et al. | |
| 2003/0191005 A1 * | 10/2003 | Coelho et al. | 494/37 |
| 2003/0232712 A1 | 12/2003 | Dolecek et al. | |
| 2004/0026341 A1 * | 2/2004 | Hogberg et al. | 210/782 |
| 2004/0058794 A1 | 3/2004 | Dolecek et al. | |
| 2004/0104182 A1 * | 6/2004 | Holmes et al. | 210/787 |
| 2004/0230152 A1 * | 11/2004 | Bainbridge et al. | 604/6.01 |
| 2008/0053203 A1 * | 3/2008 | Hogberg et al. | 73/61.44 |

FOREIGN PATENT DOCUMENTS

| | | |
|---|---|---|
| EP | 0 499891 B1 | 8/1992 |
| EP | 0 771 569 B1 | 5/1997 |
| WO | WO92/00145 A1 | 1/1992 |
| WO | WO01/97943 A1 | 12/2001 |
| WO | WO2004/018021 A2 | 3/2004 |
| WO | WO2004/018021 A3 | 3/2004 |
| WO | WO 2004018021 A2 * | 3/2004 |

OTHER PUBLICATIONS

EP Application No. 09005624.3-2310, "Extended Search Report", Jun. 18, 2009.

* cited by examiner

APPARATUS FOR SEPARATING A VOLUME OF WHOLE BLOOD INTO AT LEAST THREE COMPONENTS

CROSS-REFERENCE TO RELATED APPLICATIONS

This application is a continuation of International Application No. PCT/US2005/044821, filed Dec. 12, 2005, which claims the benefit of U.S. Provisional Application No. 60/639,497, filed Dec. 28, 2004.

FIELD OF THE INVENTION

The invention concerns an apparatus and a method for separating a volume of whole blood into at least three components.

BACKGROUND OF THE INVENTION

Whole blood comprises cellular components, namely red blood cells (erythrocytes), white blood cells (leukocytes) and platelets (thrombocytes), which are suspended in a liquid component, plasma, consisting of water and solutes (in particular proteins, electrolytes and metabolites). The white blood cells comprise mononuclear cells (lymphocytes, monocytes, stem cells) and polymorphonuclear cells (granulocytes, comprising neutrophils, eosinophils and basophils).

Each kind of blood cell performs a specific function: red blood cells transport oxygen from the lungs to body cells and carbon dioxide from body cells to the lungs; white blood cells are part of the immune system, which protects the body against microorganisms and foreign matter; platelets help prevent blood loss by forming a plug at the site of vascular injuries.

Plasma proteins also perform specific functions: clotting proteins (coagulation factors) assist in clot formation by holding the platelet plug in place, globulins (antibodies) neutralize foreign substances as part of the immune response, and albumin helps maintain the water content and the viscosity of the plasma, both of which are necessary to keep a normal blood pressure.

Because of the specificity of the functions fulfilled by the blood cells and by the plasma proteins, it is customary today to infuse or inject into a patient only the blood component or the fraction thereof (e.g. coagulation factors) needed by the patient to address a particular surgical or medical condition. Whole blood may still be infused to replace blood lost during trauma or surgery, however, most of the time, only the blood component missing or destroyed by disease or chemotherapy is administered.

The whole blood or blood components or any fraction thereof that are infused or injected into patients originate from healthy donors (who can be the future recipients of the blood product, in case of an autologous donation). A blood donation generally consists of either about 450 ml (one pint) or about 500 ml of whole blood.

In accordance with the current infusion practices mentioned above, donated whole blood is usually separated into two or three blood components, namely plasma and red blood cells, or plasma, red blood cells and platelets.

The separation of whole blood into two blood products includes a centrifugation phase, by which blood is separated into plasma and packed red blood cells, and an optional filtration phase, by which platelets and white blood cells are removed from the packed red blood cells.

The separation of whole blood into three blood products includes a centrifugation phase, by which blood is separated into a first component mainly comprising plasma, a second component mainly comprising platelets and a third component mainly comprising red blood cells. In a further filtration stage, which is optional, white blood cells are removed from the packed red blood cells. Platelets separated from four to six blood donations are pooled to form a transfusion dose and white blood cells are removed therefrom by filtration.

It is important to remove white blood cells from whole blood and blood components (platelets, packed red blood cells) for the following reasons, in particular: during storage, white blood cells release cytokines, which, when transfused into a patient can cause febrile non-hemolytic transfusion reactions. Also, after multiple transfusions, some patient develop antibodies to human leukocytes antigens (HLA) that react to HLA on the membrane of donor white cells. HLA antibodies also can cause transfusion reactions in patients who receive multiple transfusions. White blood cells are also responsible for the transmission of diseases.

International patent application WO 2004/018021 describes a method and an apparatus for separating a volume of whole blood into either a plasma component and a red blood cell component; or a plasma component, a red blood cell component and a platelet component.

The apparatus comprises a centrifuge adapted to cooperate with an annular separation bag for whole blood, which is connected to either a plasma component bag and a red blood cell component bag or a plasma component bag, a red blood cell component bag and a platelet component bag.

The centrifuge includes: a rotor for spinning the separation bag and centrifuging the whole blood contained therein, the rotor having a turntable for supporting the separation bag and a central compartment for containing the component bags connected to the separation bag; and a squeezing system for squeezing the separation bag and causing the transfer of the plasma component from the separation bag into the plasma component bag, of the red blood cell component into the red blood cell component bag and, as the case may be, of the platelet component into the platelet component bag.

According to the method described in International patent application WO 2004/018021, the removal of white blood cells (so-called "leukoreduction") from the various blood components can be performed either before centrifugation of the whole blood or after separation of the whole blood into two or three components. In the pre-centrifugation removal process, the white blood cells (and, as the case may be platelets) are removed by filtration from the whole blood during the transfer thereof from a collection bag into the separation bag. In the post-separation process, white blood cells, (and as the case may be platelets), are removed by filtration from the red blood cell component during the transfer thereof from a transfer bag into a red blood cell product bag.

BRIEF SUMMARY OF THE INVENTION

It has been observed during the research work that has led to the present invention that the filtration, through a conventional filter, of a red blood cell component in order to remove therefrom white blood cells and, as the case may be, platelets, may result in the clogging of the filter and/or in the presence of residual white blood cells in the filtered red blood cell products, in particular when a blood donation, instead of being processed within a few hours after its collection, is stored at room temperature for up to twenty four hours before being processed.

One object of the invention is to design a method and an apparatus for separating whole blood that would allow for the preparation of transfusable products containing less than a predetermined amount of residual white blood cells.

According to one embodiment of the invention, a method for separating a volume of whole blood contained in a separation bag into at least three components, comprises: centrifuging the separation bag so as to separate therein a first inner layer comprising plasma, a second intermediate layer comprising platelets, a third intermediate layer comprising lymphocytes, monocytes and granulocytes and a fourth outer layer comprising red blood cells, wherein at least the third and fourth layers partially overlap; transferring, into a plasma component bag connected to the separation bag, a plasma component substantially comprising a first fraction of the first layer; and transferring, into a mononuclear cell component bag connected to the separation bag, a mononuclear cell component comprising at least a fraction of the third layer comprising lymphocytes and monocytes.

Other characteristics of the method according to the invention are as follows.

The mononuclear cell component further comprises a second fraction of the first layer and the second layer.

The method further comprises, after transferring the mononuclear cell component into the mononuclear cell component bag, transferring, into a red blood cell component bag connected to the separation bag, a red blood cell component comprising the fourth layer and a fraction of the third layer comprising granulocytes.

The method further comprises filtering the red blood cell component during the transfer thereof into the red blood cell component bag so as to substantially remove therefrom granulocytes, and residual monocytes and lymphocytes.

The method further comprises, before transferring the red blood cell component from the separation bag into the red blood cell component bag, transferring a volume of storage solution from the red blood cell component bag into the separation bag. Transferring the red blood cell component from the separation bag into the red blood cell component bag occurs after stopping centrifuging the separation bag. The red blood cell component is transferred by gravity from the separation bag into the red blood cell component bag.

The method further comprises, after transferring the plasma component into the plasma component bag, transferring, into a platelet component bag connected to the separation bag, a platelet component comprising a fraction of the second layer and the fraction of the first layer remaining in the separation bag after the transfer of the plasma component into the plasma component bag.

The method further comprises mixing the fraction of the first layer and the fraction of the second layer of which the platelet component is comprised so as to suspend platelets in plasma before transferring the platelet component into the platelet component bag. The platelet component is transferred into the platelet component bag at at least two successive flow rates, a first flow rate being faster than a second flow rate.

The method further comprises stopping centrifuging the separation bag after transferring the mononuclear cell component into the mononuclear cell component bag.

The invention presents at least the following advantages. The filtration, through a conventional leukoreduction filter (a filter for removing white blood cells), of a red blood cell component substantially devoid of mononuclear cells and, as the case may be, of platelets, occurs without clogging of the filter and results in a red blood cell product in which the residual white blood cells are less than the standard set by the MBB (American Association of Blood Banks). This result is achieved even if a volume of whole blood kept at room temperature is separated into various components one day after its collection from a donor. The time needed for filtering, through a conventional leukoreduction filter, a red blood cell component substantially devoid of mononuclear cells and, as the case may be, of platelets, is substantially shorter than the time currently needed for filtering a red blood cell component comprising red blood cells, white blood cells and, as the case may be, platelets. The mononuclear cell component isolated by centrifugation in accordance with the invention constitutes a valuable product, from which, for example, substances of therapeutic interest like interferons can be extracted (interferons are cytokines that attack virally infected cells).

As mentioned above, the packed red blood cells currently prepared are not always filtered before infusion into a patient. This is for economic reason, since filtering blood entails a cost. In this respect, the red blood cell component obtained by the method according to the invention, which is substantially devoid of mononuclear cells, is a far better product to be infused without filtration than the packed red cells separated by the conventional process.

According to one embodiment of the invention, a method for separating a volume of whole blood contained in a separation bag into at least a plasma component, a mononuclear cell component and a red blood cell component, the separation bag being fluidly connected at least to a plasma component bag and a mononuclear cell component bag, comprises: spinning the separation bag around a rotation axis at a first rotation speed so as to separate therein a first inner layer comprising plasma, a second intermediate layer comprising platelets, a third intermediate layer comprising lymphocytes, monocytes and granulocytes and a fourth outer layer comprising red blood cells, wherein at least the third and fourth layers partially overlap; blocking a fluid communication between the separation bag and the mononuclear cell bag; allowing a fluid communication between the separation bag and the plasma component bag; squeezing the separation bag until red blood cells are detected at a first distance from the axis of rotation so as to transfer, into the plasma component bag, a plasma component comprising a first fraction of the first layer; blocking a fluid communication between the separation bag and the plasma component bag; allowing a fluid communication between the separation bag and the mononuclear cell component bag; and squeezing the separation bag so as to transfer, into the mononuclear cell component bag, a mononuclear cell component comprising at least a fraction of the third layer comprising lymphocytes and monocytes.

Other characteristics of this method are as follows. The mononuclear cell component further comprises a second fraction of the first layer, the second layer, and a fraction of the fourth layer. The mononuclear cell component transferred into the mononuclear cell component bag has a predetermined volume. The volume of whole blood is about 450 ml and the volume of the mononuclear cell component is comprised between about 10 ml and about 15 ml. The volume of whole blood is about 450 ml and the volume of the mononuclear cell component is comprised between about 50 ml and about 60 ml.

The method further comprises, after transferring the mononuclear cell component into the mononuclear cell component bag, stopping spinning the separation bag.

The method further comprises, after squeezing the separation bag so as to transfer the plasma component into the plasma component bag: mixing the second layer and a second fraction of the first layer remaining in the separation bag so as to prepare a platelet component comprising platelets of the second layer suspended in the second fraction of the first layer; blocking a fluid communication between the separation bag and the plasma component bag and between the separation bag and the mononuclear cell component bag; allowing a fluid communication between the separation bag and a platelet component bag connected to the separation bag; and squeezing the separation bag until red blood cells are detected at a second distance from the axis of rotation so as to transfer the platelet component into the platelet component bag, wherein the second distance is shorter than the first distance. Mixing the second layer and a second fraction of the first layer remaining in the separation bag so as to prepare a platelet component comprises: decreasing the rotation speed from the first rotation speed to a second rotation speed so as to mix the second fraction of the first layer, the second layer, the third layer and a fraction of the fourth layer; and increasing the rotation speed from the second rotation speed to a third rotation speed so as to separate the platelet component from the third layer and the fourth layer, the third rotation speed being lower than the first rotation speed. Squeezing the separation bag so as to transfer the platelet component into the platelet component bag comprises: squeezing the separation bag so as to transfer the platelet component at a first flow rate until red blood cells are detected at a second distance from the axis of rotation, the second distance being smaller than the first distance; squeezing the separation bag so as to transfer the platelet component at at least a second flow rate lower than the first flow rate, following the detection of red blood cells at the second distance from the axis of rotation; and stopping squeezing the separation bag following the detection of red blood cells at a third distance from the axis of rotation, the third distance being smaller than the second distance.

The method further comprises, after transferring the mononuclear cell component into the mononuclear cell component bag, transferring, into a red blood cell component bag connected to the separation bag, a red blood cell component comprising the fourth layer and a fraction of the third layer comprising granulocytes.

The method further comprises filtering the red blood cell component during the transfer thereof into the red blood cell component bag so as to substantially remove therefrom granulocytes, and residual monocytes and lymphocytes.

According to one embodiment of the invention, a red blood cell component is extracted from a volume of whole blood through the steps of: centrifuging the volume of whole blood in a separation bag so as to separate therein a first inner layer comprising plasma, a second intermediate layer comprising platelets, a third intermediate layer comprising lymphocytes, monocytes and granulocytes and a fourth outer layer comprising red blood cells, wherein at least the third and fourth layers partially overlap; and removing from the separation bag the first layer, the second layer and a fraction of the third layer containing most of the lymphocytes and the monocytes. The red blood cell component may be extracted through the additional step of filtering the fourth layer and the remaining portion of the third layer so as to substantially remove therefrom the granulocytes, and the residual monocytes and lymphocytes. The red blood cell component may be extracted through the additional step of transferring a volume of storage solution for red blood cells into the separation bag before the step of filtering the fourth layer and the remaining portion of the third layer.

According to one embodiment of the invention, a mononuclear cell component is extracted from a volume of whole blood through the steps of: centrifuging the volume of whole blood in a separation bag so as to separate therein a first inner layer comprising plasma, a second intermediate layer comprising platelets, a third intermediate layer comprising lymphocytes, monocytes and granulocytes and a fourth outer layer comprising red blood cells, wherein at least the third and fourth layers partially overlap; removing from the separation bag at least a first fraction of the first layer; and removing from the separation bag a mononuclear cell component comprising at least a fraction of the third layer comprising lymphocytes and monocytes.

The mononuclear cell component may further comprise a second fraction of the first component and the second component. The mononuclear cell component may be extracted through the additional step of removing from the separation bag the second layer and a second fraction of the first layer remaining in the separation bag after the step of removing the first fraction of the first layer.

According to one embodiment of the invention, an apparatus for separating a volume of whole blood contained in a separation bag into at least a plasma component, a mononuclear cell component and a red blood cell component, comprises: a rotor for spinning the separation container around a rotation axis of the rotor; a first valve member mounted on the rotor for interacting with a tube connecting the separation bag to the plasma component bag and selectively allowing or blocking a fluid flow therethrough; a second valve member mounted on the rotor for interacting with a tube connecting the separation bag to the mononuclear cell component bag and selectively allowing or blocking a fluid flow component therethrough; at least one sensor for detecting red blood cells in the separation bag at a distance from the rotation axis of the rotor; a fluid transfer system for causing the transfer of the plasma component from the separation bag into the plasma component bag and the transfer of the mononuclear cell component from the separation bag into the mononuclear cell component bag; a memory for storing at least one centrifugation speed allowing for the sedimentation of a volume of whole blood into a first inner layer comprising plasma, a second intermediate layer comprising platelets, a third intermediate layer comprising lymphocytes, monocytes and granulocytes and a fourth outer layer comprising red blood cells, wherein at least the third and fourth layers partially overlap; and a control unit programmed: for receiving an information from the at least one sensor, and the at least one centrifugation speed from the memory; for causing the rotor to rotate at the at least one centrifugation speed; for causing the first valve member to open the tube connected to the plasma component bag and the second valve member to close the tube connected to the mononuclear cell component bag, when the volume of whole blood has sedimented in the separation bag; for causing the fluid transfer system to transfer into the plasma component bag a plasma component comprising a first fraction of the fourth layer; for causing, when red blood cells are detected by the at least one sensor, the fluid transfer system to stop transferring a content of the separation bag, the first valve member to close the tube connected to the plasma component bag and the second valve member to open the tube connected to the mononuclear cell component bag; and for causing the fluid transfer system to transfer, into the mononuclear cell component bag, a mononuclear cell component having a predetermined volume and comprising at least a fraction of the third layer comprising lymphocytes and monocytes.

The apparatus may further comprise: a third valve member mounted on the rotor for interacting with a tube connecting the separation bag to a platelet component bag and selectively allowing or blocking a fluid flow component therethrough; and one additional sensor for detecting red blood cells in the separation bag at a distance from the rotation axis of the rotor smaller than the distance at which the at least one sensor is located, wherein the control unit is further programmed: for causing, after the transfer of the plasma component into the plasma component bag, a decrease of the rotation speed of the rotor from the first rotation speed to a second rotation speed so as to a mix a second fraction of the first layer remaining in the separation bag with the second layer, the third layer and an inner layer of the fourth layer; for causing, after the mixing of the second fraction of the first layer with the second layer, the third layer and the inner layer of the fourth layer is completed, an increase of the rotation speed of the rotor from the second rotation speed to a third rotation speed so as to separate a platelet component from the third and fourth layers, the platelet component comprising platelets suspended in the second fraction of the fourth layer, the third speed being lower than the first speed; for causing, when the platelet component is separated, the first valve member to close the tube connected to the plasma component bag, the second valve member to close the tube connected to the mononuclear cell component bag, and the third valve member to open the tube connected to the platelet component bag; and for causing the fluid transfer system to transfer the platelet component from the separation bag into the platelet component bag at least until the additional sensor detects red blood cells.

The fluid transfer system may comprise a squeezing system for squeezing the separation bag and causing the transfer of a content of the separation bag into at least one of the plasma component bag and the mononuclear cell component bag.

The fluid transfer system may comprise a pumping system for causing the transfer of a content of the separation bag into at least one of the plasma component bag and the mononuclear cell component bag.

BRIEF DESCRIPTION OF THE DRAWINGS

Other features and advantages of the invention will appear from the following description and accompanying drawings, which are to be considered exemplary only. In the accompanying drawings.

DETAILED DESCRIPTION OF THE INVENTION

Figure 1:
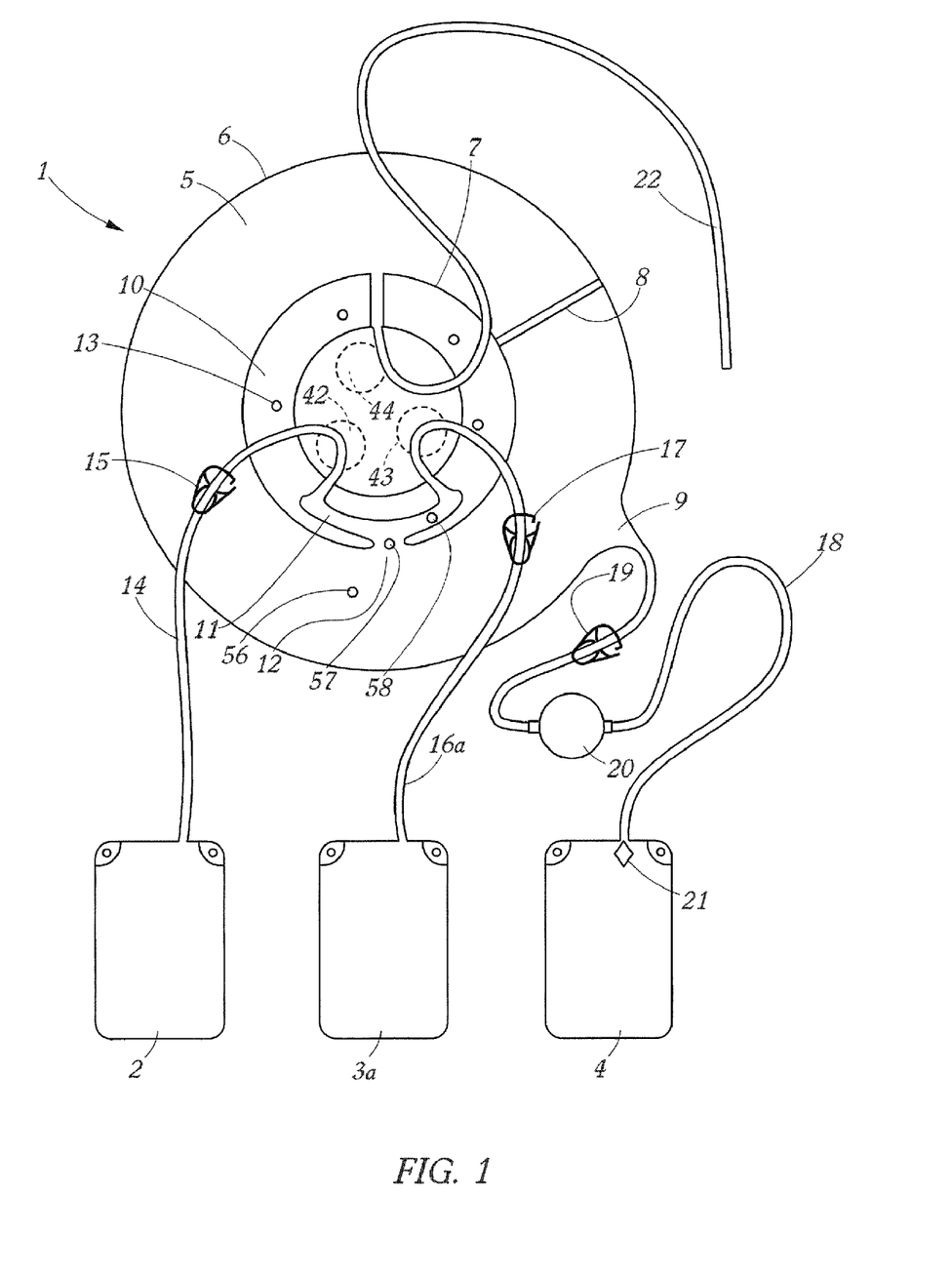
FIG. 1 is a schematic view of a first set of separation bags designed for cooperating with a separation apparatus according to the invention.

FIG. 1 shows an example of a set of bags adapted to the separation of whole blood into a plasma component (essentially comprising plasma), a red blood cell component (essentially comprising red blood cells and granulocytes) and a mononuclear cell component (comprising monocytes and lymphocytes, as well as plasma, platelets and red blood cells). This bag set comprises a flexible separation bag 1 and three flexible satellite bags 2, 3a, 4 connected thereto. The separation bag 1 comprises a partially annular separation chamber 5 having a substantially circular outer edge 6, an inner circular edge 7 and a radial wall 8 extending from the inner edge 7 to the outer edge 6 so that the chamber 5 has a shape of a broken ring. The outer circular edge 6 and the inner circular edge 7 of the separation chamber 5 are substantially concentric. The separation chamber 5 also comprises a funnel like extension 9 protruding outwardly from its outer edge 6 for helping evacuate a content of the separation chamber 5 into the third satellite bag 4. The separation bag 1 further comprises a semi-flexible disk-shaped connecting element 10 that is connected to the inner edge 7 of the annular chamber 5. The disk-shaped connecting element 10 comprises a substantially semi-circular distribution channel 11 embedded therein, which communicates through a passage 12 with the annular chamber 5. The disk-shaped connecting element 10 comprises a series of holes 13 for connecting the separation bag 1 to the rotor of a centrifuge.

The first satellite bag 2 is intended for receiving a plasma component. It is flat and substantially rectangular. It is connected by a first tube 14 to the separation bag 1. The first tube 14, which is fitted with a clamp 15, has a first end connected to the upper edge of the first satellite bag 2 and a second end connected to a first end of the distribution channel 11.

The second satellite bag 3a is intended for receiving a mononuclear cells component. The second satellite bag 3a is flat and substantially rectangular. It is connected by a second tube 16a to the separation bag 1. The second tube 16a, which is fitted with a clamp 17, has a first end connected to the upper edge of the second satellite bag 3a and a second end connected to a second end of the distribution channel 11.

The third satellite bag 4 is intended for receiving a red blood cell component. It is flat and substantially rectangular. It is connected by a third tube 18 to the separation bag 1. The third tube 18 has a first end connected to the upper edge of the third satellite bag 4 and a second end connected to the tip of the funnel like extension 9 of the separation chamber 5. It comprises two segments respectively connected to the inlet and the outlet of a leukoreduction filter 20. The tube segment connected to the separation bag 1 is fitted with a clamp 19. The filter may be, for example, a filter of the type RC2D manufactured by Pall Corporation. Such a filter comprises a disk-shaped casing to which radial inlet and outlet ports are connected, in diametral opposition. The casing, which is made of polycarbonate (GE Lexan HF 1140), has an internal volume of about 33 ml. It is filled up with a filtering medium composed of multiple layers of a non-woven web of polyester fibers (about two micron diameter). The third satellite bag 4 contains a volume of storage solution for red blood cells. A plug 21 removable from within the third satellite bag 4 (so-called "frangible pin", for example) blocks a liquid flow through the product tube 18 and prevents the storage solution from flowing from the third satellite bag 4 into the separation bag 1.

The bag set further comprises a transfer tube 22 that is connected at one end to the inner edge 7 of the separation bag 1 and that is closed at the other end. The transfer tube 22 is used to connect a collection bag to the separation bag 1 and transfer therein the content (anti-coagulated whole blood donation) of the collection bag.

Variants of the separation bag 1 may include: a separation chamber 5 having an outer circular edge 6 and/or an inner circular edge 7 that are eccentric; a separation chamber 5 that does not comprise any radial wall extending from the inner edge 7 to the outer edge 6 so that the chamber 5, instead of being C-shaped, is annular; a separation chamber 5 having any shape including an inner edge and an outer edge (the inner edge being closer to the axis of the rotor of a centrifuge than the outer edge, when the separation bag is mounted on the rotor of a centrifuge), for example the shape of a portion of annulus delimited by two lateral radial edge or a rectangular shape. In this variant, all the satellite bags may be connected to the inner edge of the separation bag.

Also the separation bag 1 can be shaped so as to fit either on a flat support surface or on a frusto-conical support surface of the rotor of a centrifuge.

Figure 2:
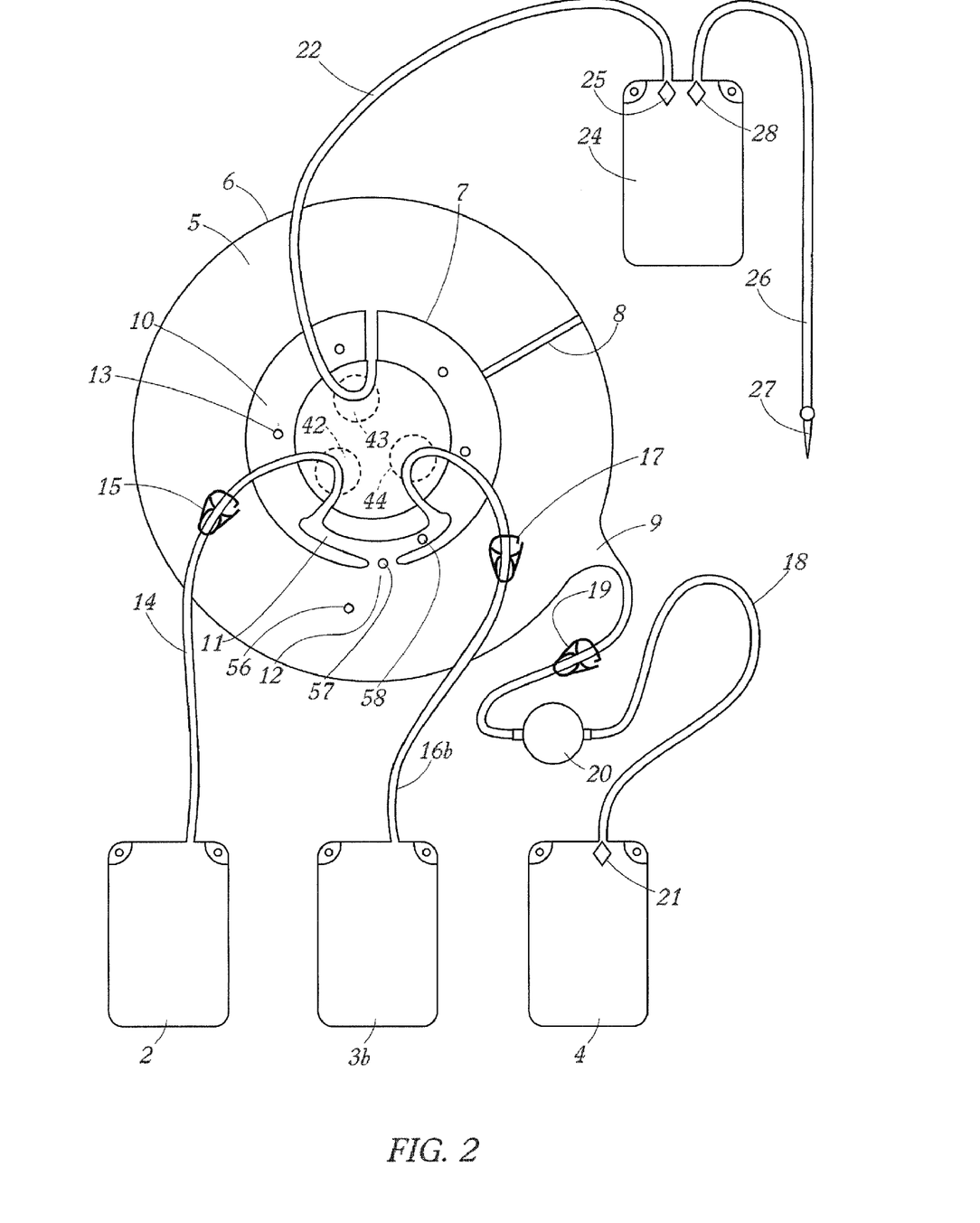
FIG. 2 is a schematic view of a second set of separation bags designed for cooperating with a separation apparatus according to the invention.

FIG. 2 shows an example of a set of bags adapted to the separation of whole blood into a plasma component (comprising essentially plasma), a platelet component comprising essentially platelets), a red blood cell component (comprising essentially red blood cells and granulocytes) and a mononuclear cell component (comprising monocytes and lymphocytes, as well as red blood cells and platelets). This bag set comprises a separation bag 1 and four satellite bags 2, 3*b*, 4, 24 connected thereto.

The separation bag 1 and the three satellite bags 2, 3*b*, 4 are identical to those shown in FIG. 1, except that the satellite bag 3*b* is intended to receive the platelet component instead of the mononuclear cells component.

The specificity of the bag set of FIG. 2 resides in the fourth satellite bag 24, which has two purposes and is successively used as a collection bag and as a mononuclear cell component bag. The fourth satellite bag is intended for initially receiving a volume of whole blood from a donor (usually about 450 ml) before the separation process, and the mononuclear cells component during the separation process. The fourth satellite bag 24 is flat and substantially rectangular. It is connected to the separation bag 1 by a transfer tube 22 having a first end connected to the upper edge of the fourth satellite bag 24 and a second end connected to the inner edge 7 of the annular chamber 5. The fourth satellite bag 24 contains a volume of anti-coagulant solution (typically about 63 ml of a solution of citrate phosphate dextrose for a blood donation of about 450 ml). A plug 25 removable from within the fourth satellite bag 24 (so-called "frangible pin", for example) blocks a liquid flow through the transfer tube 22 and prevents the anti-coagulant solution from flowing from the fourth satellite bag 24 into the separation bag 1.

The bag set of FIG. 2 further comprises a collection tube 26 that is connected at one end to the upper edge of the fourth satellite bag 24 and comprises, at the other end, a needle protected by a sheath 27. A frangible pin 28 removable from within the fourth satellite bag 24 plugs the downstream end of the collection tube 26 and prevents the anti-coagulant solution from flowing out of the fourth satellite bag 24 through the collection tube 26.

A variant of the bag set of the FIG. 2 may comprise a fifth satellite bag connected to the distribution channel specifically intended for the mononuclear cells component.

The bags and the tubes of the first and second bag sets shown in FIGS. 1 and 2 are all made of flexible plastic material appropriate to contact blood and blood components.

Figure 3:
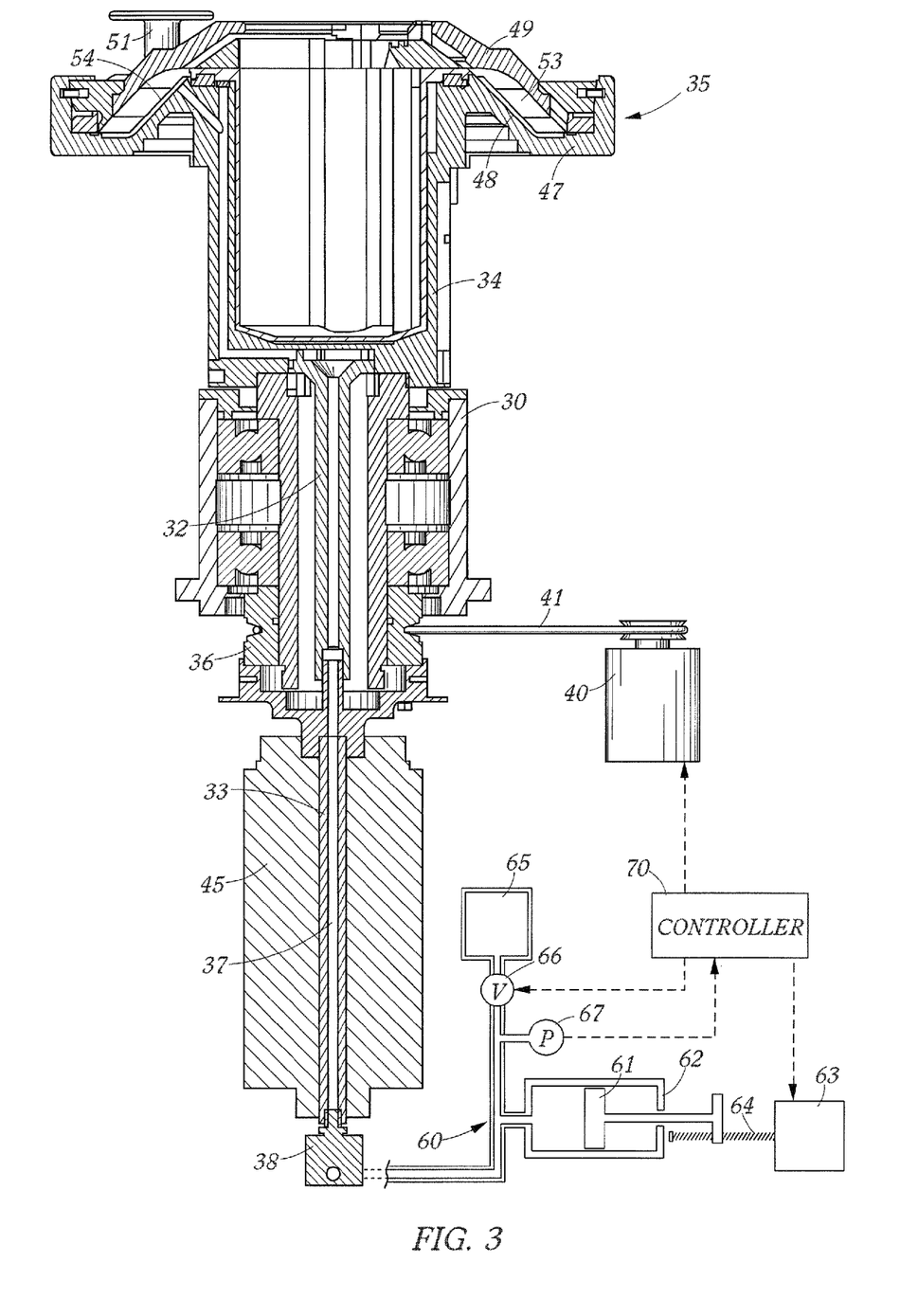
FIG. 3 is a schematic view, partly in cross-section, of a separation apparatus according to the invention.
Figure 4:
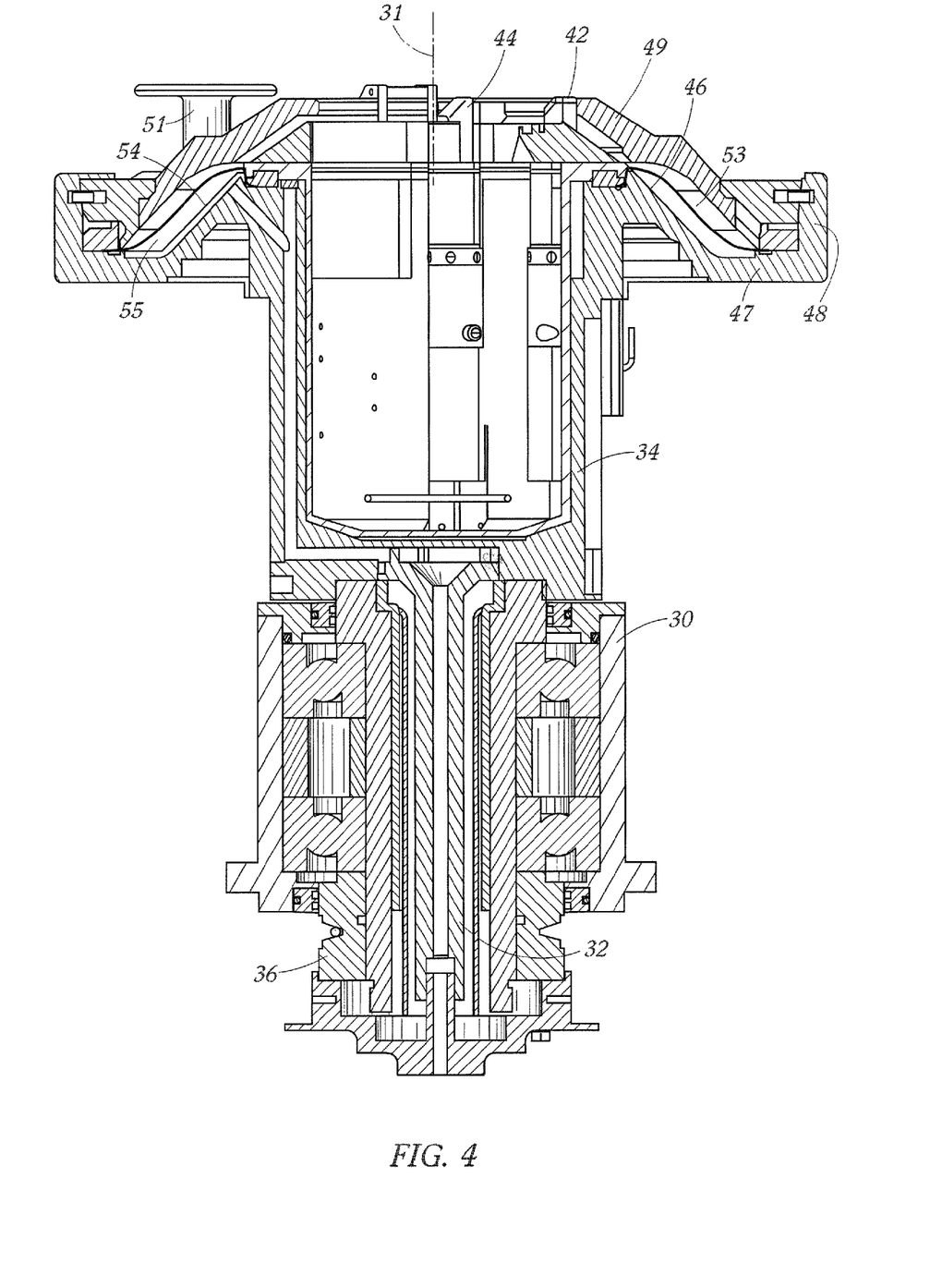
FIG. 4 is a cross-section view of the rotor of a separation apparatus according to the invention.
Figure 5:
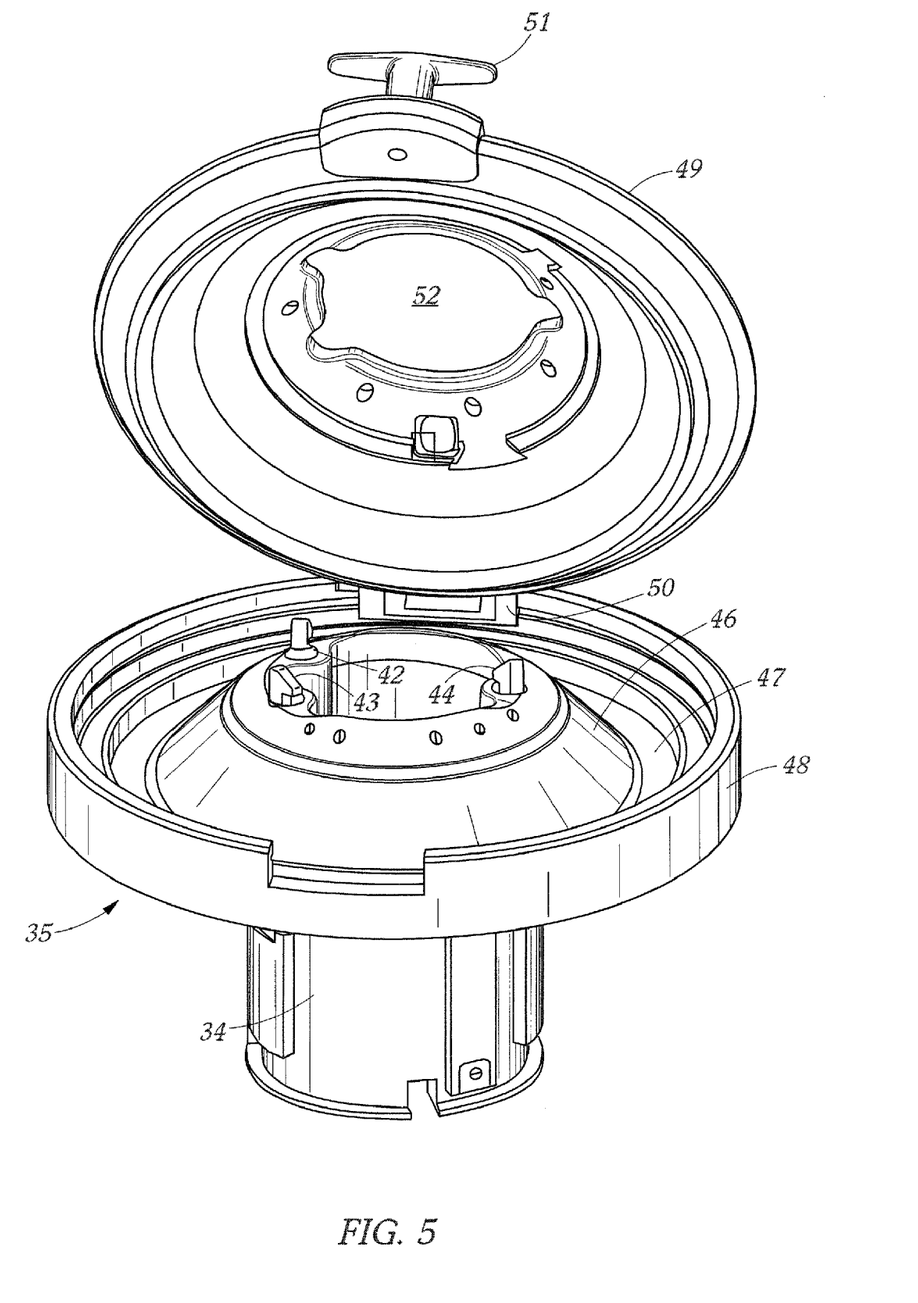
FIG. 5 is a perspective view of the upper part of the rotor of the separation apparatus of FIG. 4.

FIGS. 3, 4, 5 show an apparatus for separating a volume of whole blood by centrifugation. The apparatus comprises a centrifuge adapted for receiving either set of separation bags shown in FIGS. 1 and 2, and a fluid transfer system for causing the transfer of separated components into the satellite bags.

The centrifuge comprises a rotor that is supported by a bearing assembly 30 allowing the rotor to rotate about a vertical central axis 31. The rotor comprises a cylindrical rotor shaft 32, 33, a cylindrical container 34 for containing satellite bags (component bags and, as the case may be, a collection bag), which is connected to the rotor shaft 32, 33 at the upper end thereof so that the longitudinal axis of the rotor shaft 32, 33 and the longitudinal axis of the container 34 are aligned with the central axis 31 of the rotor, and a circular turntable 35 for supporting a separation bag, which is connected to the container 34 at the upper end thereof so that the central axis of the turntable 35 is aligned with the central axis 31 of the rotor. The rotor shaft comprises a first upper portion 32 and a second lower portion 33. The upper portion 32 of the shaft extends in part through the bearing assembly 30. A pulley 36 is connected to the lower end of the upper portion 32 of the shaft.

The centrifuge further comprises a motor 40 coupled to the rotor by a belt 41 engaged in a groove of the pulley 36 so as to rotate the rotor about the central vertical axis 31.

The separation apparatus further comprises a first, second and third pinch valve members 42, 43, 44 that are mounted on the rotor for selectively blocking or allowing a flow of liquid through a flexible plastic tube, and selectively sealing and cutting a plastic tube. Each pinch valve member 42, 43, 44 comprises an elongated cylindrical body and a head having a groove that is defined by a stationary upper jaw and a lower jaw movable between an open and a closed position, the groove being dimensioned so that one of the tubes 14, 16*a*, 16*b*, 22 of the bag sets shown in FIGS. 1 and 2 can be snuggly engaged therein when the lower jaw is in the open position. The elongated body contains a mechanism for moving the lower jaw and it is connected to a radio frequency generator that supplies the energy necessary for sealing and cutting a plastic tube. The pinch valve members 42, 43, 44 are mounted inside the cylindrical container 34, adjacent the interior surface thereof, so that their longitudinal axis is parallel to the central axis 31 of the rotor and their heads protrude above the rim of the container 34. The position of the pinch valve members 42, 43, 44 with respect to the separation bag 1 and the tubes 14, 16*a*, 16*b*, 22 connected thereto when the separation bag 1 is mounted on the turntable 35 is shown in doted lines in FIGS. 1 and 2. Electric power is supplied to the pinch valve members 42, 43, 44 through a slip ring 45 that is mounted around the lower portion 33 of the rotor shaft.

The turntable 35 comprises a central frusto-conical portion 46, the upper, smaller edge of which is connected to the rim of the container 34, an annular flat portion 47 connected to the lower, larger edge of the frusto-conical portion 46, and an outer cylindrical flange 48 extending upwards from the outer periphery of the annular portion 47. The turntable 35 further comprises a vaulted circular lid 49 that is secured to the flange 48 by a hinge 50 so as to pivot between an open and a closed position. The lid 49 is fitted with a lock 51 by which it can be blocked in the closed position. The lid 49 comprises a large cut-out 52 in its upper part that gives access to the cylindrical container 34 of the rotor. The lid 49 has an annular interior surface that is so shaped that, when the lid 49 is in the closed position, it defines with the frusto-conical portion 46 and the annular flat portion 47 of the turntable 38 a frusto-conical annular compartment 53 having a radial cross-section that has substantially the shape of a parallelogram. The frusto-conical annular compartment 53, later the "separation compartment", is intended for containing the separation bag 1 shown in FIGS. 1 and 2.

The fluid transfer system for causing the transfer of a content of the separation bag 1 (e.g. the separated components) into the satellite bags comprises a squeezing system for squeezing the separation bag within the separation compartment 53. The squeezing system comprises a flexible annular diaphragm 54 that is so shaped as to line the frusto-conical portion 46 and the annular flat portion 47 of the turntable 35, to which it is secured along its smaller and larger circular edges. The fluid transfer system further comprises a hydraulic pumping system 60 for pumping a hydraulic liquid in and out an expandable hydraulic chamber 55 defined between the flexible diaphragm 54 and the turntable 35, via a duct 37 extending through the rotor from the lower end of the lower portion 33 of the rotor shaft to the turntable 35. The pumping system 60 comprises a piston pump having a piston 61 movable in a hydraulic cylinder 62 fluidly connected via a rotary fluid coupling 38 to the rotor duct 37. The piston 61 is actuated by a stepper motor 63 that moves a lead screw 64 linked to the piston rod. The hydraulic cylinder 62 is also connected to a hydraulic liquid reservoir 65 having an access controlled by a valve 66 for selectively allowing the introduction or the withdrawal of hydraulic liquid into and from a hydraulic circuit including the hydraulic cylinder 62, the rotor duct 37 and the expandable hydraulic chamber 55. A pressure gauge 67 is connected to the hydraulic circuit for measuring the hydraulic pressure therein.

A variant of the fluid transfer system may comprise one or several peristaltic pumps mounted on the rotor and so designed as to cooperate with the tubes connecting the separation bag to the satellite bags and cause a flow of liquid therethrough.

The separation apparatus further comprises three sensors 56, 57, 58 for detecting characteristics of the separation process occurring within a separation bag when the apparatus operates. The three sensors 56, 57, 58 are embedded in the lid 49 at different distances from the rotation axis of the rotor, a first sensor 56 being the farthest to the rotation axis, a third sensor 58 being the closest to the rotation axis and a second sensor 57 occupying an intermediate position. When the lid 49 is closed, the three sensors 56, 57, 58 face the separation bag 1 as shown in FIGS. 1 and 2. The first and second sensors 56, 57 are generally in the pathway of any component flowing from the separation chamber 5 to the first and second satellite bags 2 and 3b, and the third sensor 58 is in the pathway of any component flowing from the separation chamber 5 to the second satellite bag 3b. The first sensor 56 (later the "bag sensor") is embedded in the lid 49 so as to be positioned over the separation chamber 5, at about one third of the breadth of the separation chamber from the inner edge 6 thereof, slightly outside of the passage 12 between the separation chamber 5 and the distribution channel 11. The bag sensor 56 is able to detect red blood cells in a liquid. The second sensor 57 (later the "bay sensor") is embedded in the lid 49 so as to be positioned over the passage 12 between the separation chamber 5 and the distribution channel 11. The bay sensor 57 is able to detect the presence or absence of liquid in the distribution channel 11 as well as to detect red blood cells in a liquid. The third sensor 58 (later the "channel sensor") is embedded in the lid 49 so as to be positioned over the distribution channel 11. The channel sensor 58 is able to detect the presence or absence of liquid in the distribution channel 11 as well as to detect red blood cells in a liquid. Each sensor 56, 57, 58 can comprise a photocell including an infra-red LED and a photo-detector.

The separation apparatus further comprises a controller 70 including a control unit (microprocessor) and a memory for providing the microprocessor with information and programmed instructions relative to various separation protocols and to the operation of the apparatus in accordance with such separation protocols. In particular, the microprocessor is programmed for receiving information relative to the centrifugation speed(s) at which the rotor is to be rotated during the various stages of a separation process, and information relative to the various transfer flow rates at which separated components are to be transferred from the separation bag 1 into the satellite bags 2, 3a, 3b, 24. The information relative to the various transfer flow rates can be expressed, for example, as hydraulic liquid flow rates in the hydraulic circuit, or as rotation speeds of the stepper motor 63 of the hydraulic pumping system 60. The microprocessor is further programmed for receiving, directly or through the memory, information from the pressure gauge 67 and from the photocells 56, 57, 58 and for controlling the centrifuge motor 40, the stepper motor 63, and the pinch valve members 42, 43, 44 so as to cause the separation apparatus to operate along a selected separation protocol.

An example of a first separation protocol aiming at the preparation of three blood components, namely plasma, mononuclear cells and red blood cells, from a whole blood donation, is explained below. This first separation protocol does not require the use of the third pinch valve member 44 nor of the channel sensor 58. The operation of the separation apparatus along the first separation protocol is as follows:

First stage (first protocol): a volume of anti-coagulated blood to be separated is transferred into the separation bag 1 of the bag set of FIG. 1.

After the clamps 15, 17, 19 have been closed on the tubes 14, 16a, 18 connected to the separation bag 1, a volume of anti-coagulated whole blood (usually about 500 ml) contained in a collection bag is transferred by gravity into the separation bag 1 through the transfer tube 22 connected thereto. The transfer tube 22 is sealed and cut. The separation bag 1 is mounted on the turntable 35, the product tubes 14, 16a are engaged in the first and second pinch valve members 42, 43 respectively and the satellite bags 2, 3a, 4, and the filter 20 are placed into the container 34. The pinch valve members 42, 43 are closed and the clamps 15 and 17 on the tubes 14 and 16a are opened. The clamp 19 on the tube 18 connected to the third satellite bag 4 remains closed. The lid 49 of the rotor is closed.

As a variant of this first stage, the volume of anti-coagulated whole blood is transferred into the separation bag 1 after the bag set of FIG. 1 has been mounted on the rotor of the separation apparatus.

Second stage (first protocol): the air present in the separation bag 1 is purged into the second satellite bag 3a in which the mononuclear cell component is to be later transferred.

At the onset of the second stage, the first and second pinch valve members 42, 43 are closed. The rotor is set in motion by the centrifuge motor 40 and its rotation speed increases steadily until it reaches the high centrifugation speed (for example, about 3200 RPM) at which it will rotate during the whole separation process. When the centrifugation speed reaches a predetermined intermediate value (for example, about 1000 RPM), the second pinch valve member 43 is opened (controlling the communication between the separation bag 1 and the second satellite bag 3a intended for the mononuclear cells component) and the pumping system 60 is actuated so as to pump hydraulic liquid at a constant flow rate (for example, about 240 ml/min) into the hydraulic chamber 55 and consequently squeeze the separation bag 1. The air present in the separation bag 1 is expelled into the second satellite bag 3a for the mononuclear cells component. After a predetermined period of time following the detection of a liquid by the bay sensor 57, the pumping system 60 is stopped and the pinch valve member 43 is closed.

Alternately, the air contained in the separation bag 1 could be expelled into the satellite bag 2 for the plasma component.

Third stage (first protocol): the blood within the separation chamber is sedimented to a desired level.

At the onset of this stage, the first and second pinch valve members 42, 43 are closed. The rotor is rotated at the high centrifugation speed (for example, about 3200 RPM) for a predetermined period of time (for example, about 220 seconds) that is selected so that, whatever the hematocrit of the whole blood initially transferred in the separation chamber 1, the blood sediments therein at the end of the predetermined period to a point where the hematocrit of the outer annular red blood cell layer is about 90 and the inner annular plasma layer plasma is substantially devoid of cells. In more details, at the outcome of this sedimentation stage, the separations bag 1 exhibits four layers: a first inner layer mainly comprising plasma, a second intermediate layer mainly comprising platelets, a third intermediate layer mainly comprising white blood cells (lymphocytes, monocytes and granulocytes), and a fourth outer layer mainly comprising red blood cells, wherein the first and second layer partially overlap (the granulocytes are in part embedded in the fourth layer).

Fourth stage (first protocol): a plasma component is transferred into the first satellite bag 2.

At the onset of this stage, the first and second pinch valve members 42, 43 are closed. The rotor is rotated at the same high centrifugation speed as in the sedimentation stage. After a predetermined period of time after the bag sensor 56 has stopped detecting red blood cells, which can happen before the end of the predetermined sedimentation period, the first pinch valve member 42 controlling the access to the first satellite bag 2 is opened and the pumping system 60 is actuated so as to pump hydraulic liquid at a constant flow rate (for example, about 220 ml/min) into the hydraulic chamber 55. The expanding hydraulic chamber 55 squeezes the separation bag 1 and causes the transfer of plasma into the first satellite bag 2. The pumping system 60 is stopped and the first pinch valve member 42 is closed after a predetermined period of time has elapsed following the detection of red blood cells by the bay sensor 57. A small volume of plasma (for example, about 5 ml) remains in the separation bag 1.

The transfer flow rate of the plasma component (which is directly related to the flow rate of the hydraulic fluid) is selected to be as high as possible without disturbing the platelet layer so as to avoid contaminating the plasma component with platelets.

As a variant of the fourth stage, the pumping system 60 is stopped after a predetermined period of time as elapsed following the detection of red blood cells by the bag sensor 56. A larger volume of plasma (for example, about 30 ml) consequently remains in the separation bag 1 than when the bay sensor 57 is used.

Fifth stage (first protocol): a mononuclear cells component is transferred into the second satellite bag 3a.

The fifth stage can start as soon as the first pinch valve member 42 is closed at the end of the fourth stage. At the onset of this fifth stage, the first and second pinch valve members 42, 43 are closed. The rotor is rotated at the same high centrifugation speed as previously. The second pinch valve member 43 controlling the access to the second satellite bag 3a is opened and the pumping system 60 is actuated so as to pump hydraulic liquid at a constant flow rate (for example, about 140 ml/min) into the hydraulic chamber 55. The expanding hydraulic chamber 55 squeezes the separation bag 1 and causes the transfer, into the second satellite bag 3a, of a mononuclear cells component comprising the residual volume of plasma, the platelets, lymphocytes, monocytes and a small amount of red blood cells. The pumping system 60 is stopped and the second pinch valve member 43 is closed after a predetermined volume has been transferred into the second satellite bag 3a, that is also after a predetermined amount of time has elapsed for a given hydraulic liquid flow rate. This predetermined volume of the mononuclear cells component depends in part on the residual amount of plasma in the separation bag 1 at the end of the fourth stage. For example, when the residual volume of plasma in the separation bag 1 is determined by the bay sensor 57, the predetermined volume of the mononuclear cell component can be set at about between 10 and 15 ml, including about 5 ml of plasma and about 5 ml of red bloods cells. Now, when the residual volume of plasma in the separation bag 1 is determined by the bag sensor 56, the predetermined volume of the mononuclear cell component can be set at about between 50 to 60 ml, including about 30 ml of plasma and 20 ml of red bloods cells.

Sixth stage (first protocol): the centrifugation process is ended.

The rotation speed of the rotor is decreased until the rotor stops, the pumping system 60 is actuated so as to pump the hydraulic liquid from the hydraulic chamber 55 at a high flow rate (for example, about 800 ml/min) until the hydraulic chamber 55 is empty, and the first and second pinch valve members 42, 43 are actuated so as to seal and cut the tubes 14 and 16a. The red blood cells, the granulocytes and residual monocytes and lymphocytes remain in the separation bag 1.

Seventh stage (first protocol): a red blood cell component is transferred into the third satellite bag 4.

The lid 49 of the rotor is opened and the separation bag 1 connected to the third satellite bag 4 is removed therefrom. The clamp 19 on the product tube 18 is opened. The frangible pin 21 blocking the communication between the third satellite bag 4 and the product tube 18 connected thereto is broken. The storage solution contained in the third satellite bag 4 is allowed to flow by gravity through the filter 20 and into the separation bag 1 where it is mixed with the red blood cells so as to lower the viscosity thereof. The content of the separation bag is then allowed to flow by gravity through the filter 20 and into the third satellite bag 4. The white blood cells (granulocytes and residual monocytes and lymphocytes) are trapped by the filter 20, so that the ultimate packed red blood cell component in the third satellite bag 4 is substantially devoid from white blood cells and meets the standard of the AABB (American Association of Blood Banks), which is less than $5 \times 10^6$ white blood cells per packed red blood cell component.

An example of a second separation protocol aiming at the preparation of four blood components, namely plasma, platelets, mononuclear cells and red blood cells, from a whole blood donation, is explained below. The operation of the separation apparatus along this second separation protocol is as follows:

First stage (second protocol): a volume of anti-coagulated blood to be separated is transferred into the separation bag 1 of the bag set of FIG. 2.

Before the first stage proper, a pint of whole blood has been received from a donor into the fourth satellite (collection) bag 24, in which it has been mixed with the anti-coagulant solution contained therein. The collection tube 26 has been sealed and cut.

After the clamps 15, 17, 19 have been closed on the tubes 14, 16b, 18 connected to the separation bag 1, the frangible pin 25 plugging the transfer tube 22 is broken and the anti-coagulated whole blood contained in the collection bag 24 is transferred by gravity into the separation bag 1 through the transfer tube 22. The separation bag 1 is mounted on the turntable 35, the tubes 14, 22, 16b are engaged in the first, second and third pinch valve members 42, 43, 44 respectively and the satellite bags 2, 3b, 4, 24 and the filter 20 are placed into the container 34. The pinch valve members 42, 43, 44 are closed and the clamps 15 and 17 on the tubes 14 and 16b are opened. The clamp 19 on the tube 18 connected to the third satellite bag 4 for red blood cells remains closed. The lid 49 of the rotor is closed.

As a variant of this first stage, the volume of anti-coagulated whole blood is transferred into the separation bag 1 after the bag set of FIG. 2 has been mounted on the rotor of the separation apparatus.

Second stage (second protocol): the air present in the separation bag 1 is purged into the collection bag 24 in which a mononuclear cells component is to be later transferred.

At the onset of the second stage, the three pinch valve members 42, 43, 44 are closed. The rotor is set in motion by the centrifuge motor 40 and its rotation speed increases steadily until it reaches a first, high centrifugation speed (for example, about 3200 RPM). When the centrifugation speed reaches a predetermined intermediate value (for example, about 1000 RPM), the second pinch valve member 43 is opened (controlling the communication between the separation bag 1 and the fourth satellite bag 24 intended for the mononuclear cells component) and the pumping system 60 is actuated so as to pump hydraulic liquid at a constant flow rate (for example, about 240 ml/min) into the hydraulic chamber 55 and consequently squeeze the separation bag 1. The air present in the separation bag 1 is expelled into the fourth satellite bag 24. After a predetermined period of time following the detection of a liquid by the bay sensor 57, the pumping system 60 is stopped and the pinch valve member 43 is closed.

Alternately, the air contained in the separation bag 1 can be expelled either into the first satellite bag 2 for a plasma component or into the second satellite bag 3b for a platelet component.

Third stage (second protocol): the blood within the separation chamber is sedimented to a desired level.

At the onset of this stage, the three pinch valve members 42, 43, 44 are closed. The rotor is rotated at the first high centrifugation speed (for example, about 3200 RPM) for a predetermined period of time (for example, about 220 seconds) that is selected so that, whatever the hematocrit of the whole blood initially transferred in the separation chamber 1, the blood sediments therein at the end of the predetermined period to a point where the hematocrit of the outer annular red blood cell layer is about 90 and the inner annular plasma layer plasma is substantially devoid of cells. In more details, at the outcome of this sedimentation stage, the separations bag 1 exhibits four layers: a first inner layer mainly comprising plasma, a second intermediate layer mainly comprising platelets, a third intermediate layer mainly comprising white blood cells (lymphocytes, monocytes and granulocytes), and a fourth outer layer mainly comprising red blood cells, wherein the first and second layer partially overlap (the granulocytes are in part embedded in the fourth layer).

Fourth stage (second protocol): a plasma component is transferred into the first satellite bag 2.

At the onset of this stage, the three pinch valve members 42, 43, 44 are closed. Throughout the fourth stage, the rotor is rotated at the first high centrifugation speed (for example, about 3200 RPM). After a predetermined period of time after the bag sensor 56 has stopped detecting red blood cells, which can happen before the end of the predetermined sedimentation period, the first pinch valve member 42 controlling the access to the first satellite bag 2 is opened and the pumping system 60 is actuated so as to pump hydraulic liquid at a constant flow rate (for example, about 220 ml/min) into the hydraulic chamber 55. The expanding hydraulic chamber 55 squeezes the separation bag 1 and causes the transfer of plasma into the first satellite bag 2. The pumping system 60 is stopped and the first pinch valve member 42 is closed after a predetermined period of time has elapsed following the detection of red blood cells by the bag sensor 56. A small volume of plasma (for example, between about 30 ml and 80 ml) remains in the separation bag 1.

The transfer flow rate of the plasma component (which is directly related to the flow rate of the hydraulic fluid) is selected to be as high as possible without disturbing the platelet layer so as to avoid contaminating the plasma component with platelets.

Fifth stage (second protocol): a platelet component is prepared in the separation bag 1.

The three pinch valve members 42, 43, 44 are closed. The rotation speed of the rotor is rapidly decreased from the first centrifugation speed to a second centrifugation speed (for example, from about 3200 RPM to about 1500 RPM) so as to mix an inner layer of red blood cells, the white blood cells, the platelets and the residual volume of plasma. The rotation speed of the rotor is then increased from the second centrifugation speed to a third centrifugation speed, lower that the first centrifugation speed (for example, from about 1500 RPM to about 2500 RPM), so as to separate a platelet component comprising a suspension of platelets in plasma from the other blood cells (red blood cells and white blood cells).

Sixth stage (second protocol): the platelet component is transferred into the second satellite bag 3b.

The third pinch valve member 44 controlling the access to the second satellite bag 3b is opened and the first and second pinch valve members 42, 43 are closed. The rotor is rotated at the third centrifugation speed (for example, about 2500 RPM). The pumping system 60 is actuated so as to the pump hydraulic liquid at a first flow rate into the hydraulic chamber 55 and consequently squeeze the separation bag 1 so as to cause the transfer of the platelet component into the second satellite bag 3b. The first flow rate (for example, about 140 ml/min) is substantially lower than the flow rate (for example, about 220 ml/min) at which the plasma component is transferred into the first satellite bag 2 in the fourth stage. The first transfer flow rate of the platelet component (which is directly related to the first flow rate of the hydraulic fluid) is selected so as to be high enough for preventing the suspended platelets from sedimenting, without at the same time triggering their activation.

When the bay sensor 57 detects red blood cells, the pumping system 60 is actuated so as to pump hydraulic liquid into the hydraulic chamber 55 at a second flow rate (for example 40 ml/min) that is substantially lower then the first flow rate, in order to prevent the contamination of the platelet component by red blood cells.

When the hydraulic liquid has been pumped into the hydraulic chamber 55 at the second flow rate for a predetermined period of time (for example, about 4 seconds), the pumping system 60 is actuated so as to pump the hydraulic liquid at a third flow rate (for example, about 20 ml/min) that is lower than the second flow rate, until a predetermined period of time (for example, about 12 seconds) has lapsed after the channel sensor 58 has detected red blood cells. The pumping system 60 is then stopped.

Seventh stage (second protocol): a mononuclear cells component is transferred into the fourth satellite (collection) bag 24.

The seventh stage can start as soon as the third pinch valve member 44 is closed at the end of the sixth stage. At the onset of this seventh stage, the three pinch valve members 42, 43, 44 are closed. The rotor is rotated at the third centrifugation speed (for example, about 2500 RPM). The second pinch valve member 43 controlling the access to the collection bag 24 is opened and the pumping system 60 is actuated so as to pump hydraulic liquid at a constant flow rate (for example, about 40 ml/min) into the hydraulic chamber 55. The expanding hydraulic chamber 55 squeezes the separation bag 1 and causes the transfer, into the collection bag 24, of a mononuclear cell component comprising residual platelets, lymphocytes, monocytes and a small amount of red blood cells. The pumping system 60 is stopped and the second pinch valve member 43 is closed after a predetermined period of time (for example, about 15 seconds) has lapsed.

Eighth stage (second protocol): the centrifugation process is ended.

The rotation speed of the rotor is decreased until the rotor stops, the pumping system 60 is actuated so as to pump the hydraulic liquid from the hydraulic chamber 55 at a high flow rate (for example, about 800 ml/min) until the hydraulic chamber 55 is empty, and the three pinch valve members 42, 43, 44 are actuated so as to seal and cut the tubes 14, 16b, and 22. The red blood cells, the granulocytes and residual monocytes and lymphocytes remain in the separation bag 1.

Ninth stage (second protocol): a red blood cell component is transferred into the third satellite bag 4.

The lid 49 of the rotor is opened and the separation bag 1 connected to the third satellite bag 4 is removed therefrom. The clamp 19 on the product tube 18 is opened. The frangible pin 21 blocking the communication between the third satellite bag 4 and the tube 18 connected thereto is broken. The storage solution contained in the third satellite bag 4 is allowed to flow by gravity through the filter 20 and into the separation bag where it is mixed with the red blood cells and the granulocytes so as to lower the viscosity thereof. The content of the separation bag is then allowed to flow by gravity through the filter 20 and into the third satellite bag 4. The white blood cells (granulocytes and residual monocytes and lymphocytes) are trapped by the filter 20, so that the ultimate packed red blood cell component in the third satellite bag is substantially devoid of white blood cells and meets the standard of the MBB (American Association of Blood Banks), which is less than $5\times10^6$ white blood cell per packed red blood cell component.

The transfer flow rate for the plasma component and the transfer flow rates for the platelet component may be substantially constant, as in the example described above, or they may vary and, for example, comprise a ramp or a series of small steps.

It will be apparent to those skilled in the art that various modifications can be made to the apparatus and method described herein. Thus, it should be understood that the invention is not limited to the subject matter discussed in the specification. Rather, the present invention is intended to cover modifications and variations.

The invention claimed is:

1. An apparatus for separating a volume of whole blood contained in a separation bag into at least a plasma component, a mononuclear cell component and a red blood cell component, the separation bag being fluidly connected to at least a plasma component bag and a mononuclear cell component bag, the apparatus comprising:
   a rotor for spinning the separation container around a rotation axis of the rotor;
   a container on the rotor for holding at least the plasma component bag and the mononuclear cell bag;
   a first valve member mounted on the rotor for interacting with a first tube connecting the separation bag to the plasma component bag and selectively allowing or blocking a fluid flow therethrough;
   a second valve member mounted on the rotor for interacting with a second tube connecting the separation bag to the mononuclear cell component bag and selectively allowing or blocking a fluid flow component therethrough;
   at least one sensor for detecting red blood cells in the separation bag at a distance from the rotation axis of the rotor;
   a fluid transfer system for causing the transfer of the plasma component from the separation bag into the plasma component bag and the transfer of the mononuclear cell component from the separation bag into the mononuclear cell component bag;
   a controller with a memory configured for storing at least one centrifugation speed allowing for the sedimentation of a volume of whole blood into a first inner layer comprising plasma, a second intermediate layer comprising platelets, a third intermediate layer comprising lymphocytes, monocytes and granulocytes and a fourth outer layer comprising red blood cells, wherein at least the third and fourth layers partially overlap and the granulocytes are in part embedded in the fourth layer; and
   a control unit programmed:
      for receiving an information from the at least one sensor, and the at least one centrifugation speed from the memory;
      for causing the rotor to rotate at the at least one centrifugation speed;
      for causing the first valve member to open the first tube connected to the plasma component bag and the second valve member to close the second tube connected to the mononuclear cell component bag, when the volume of whole blood has sedimented in the separation bag;
      for causing the fluid transfer system to transfer into the plasma component bag a plasma component comprising a first fraction of the first layer;
      for causing, when red blood cells are detected by the at least one sensor, the fluid transfer system to stop transferring a content of the separation bag, the first valve member to close the first tube connected to the plasma component bag and the second valve member to open the second tube connected to the mononuclear cell component bag; and
      for causing the fluid transfer system to transfer, into the mononuclear cell component bag, a mononuclear cell component having a predetermined volume and comprising at least a fraction of the third layer comprising lymphocytes and monocytes.

2. An apparatus according to claim 1, further comprising:
   a third valve member mounted on the rotor for interacting with a tube connecting the separation bag to a platelet component bag and selectively allowing or blocking a fluid flow component therethrough; and
   one additional sensor for detecting red blood cells in the separation bag at a distance from the rotation axis of the rotor smaller than the distance at which the at least one sensor is located, wherein the control unit is further programmed:
      for causing, after the transfer of the plasma component into the plasma component bag, a decrease of the rotation speed of the rotor from the first rotation speed to a second rotation speed so as to a mix a second fraction of the first layer remaining in the separation bag with the second layer, the third layer and an inner layer of the fourth layer;

for causing, after the mixing of the second fraction of the first layer with the second layer, the third layer and the inner layer of the fourth layer is completed, an increase of the rotation speed of the rotor from the second rotation speed to a third rotation speed so as to separate a platelet component from the third and fourth layers, the platelet component comprising platelets suspended in the second fraction of the first layer;

for causing, when the platelet component is separated, the first valve member to close the tube connected to the plasma component bag, the second valve member to close the tube connected to the mononuclear cell component bag, and the third valve member to open the tube connected to the platelet component bag; and for causing the fluid transfer system to transfer the platelet component from the separation bag into the platelet component bag at least until the additional sensor detects red blood cells.

3. An apparatus according to claim 1, wherein the fluid transfer system comprises a squeezing system for squeezing the separation bag and causing the transfer of a content of the separation bag into at least one of the plasma component bag and the mononuclear cell component bag.

4. An apparatus according to claim 1, wherein the fluid transfer system comprises a pumping system for causing the transfer of a content of the separation bag into at least one of the plasma component bag and the mononuclear cell component bag.

* * * * *